(12) United States Patent
Cagle et al.

(10) Patent No.: US 10,335,179 B2
(45) Date of Patent: Jul. 2, 2019

(54) SURGICAL DEVICE WITH KNIFE LOCKOUT

(71) Applicant: Ethicon Endo-Surgery, LLC, Guaynabo, PR (US)

(72) Inventors: David J. Cagle, Cincinnati, OH (US); David K. Norvell, Monroe, OH (US)

(73) Assignee: Ethicon LLC, Guaynabo, PR (US)

( * ) Notice: Subject to any disclaimer, the term of this patent is extended or adjusted under 35 U.S.C. 154(b) by 572 days.

(21) Appl. No.: 14/950,982

(22) Filed: Nov. 24, 2015

(65) Prior Publication Data

US 2017/0143362 A1 May 25, 2017

(51) Int. Cl.
*A61B 17/32* (2006.01)
*A61B 18/14* (2006.01)

(52) U.S. Cl.
CPC .. *A61B 17/320016* (2013.01); *A61B 18/1442* (2013.01); *A61B 18/1445* (2013.01); *A61B 2018/1455* (2013.01); *A61B 2505/05* (2013.01); *A61B 2560/0266* (2013.01)

(58) Field of Classification Search
None
See application file for complete search history.

(56) References Cited

U.S. PATENT DOCUMENTS

| | | | | |
|---|---|---|---|---|
| 4,520,817 | A * | 6/1985 | Green | A61B 17/07207 206/339 |
| 5,307,976 | A * | 5/1994 | Olson | A61B 17/07207 227/175.3 |
| 5,817,093 | A * | 10/1998 | Williamson, IV | A61B 17/07207 606/50 |
| 2007/0043352 | A1* | 2/2007 | Garrison | A61B 18/1445 606/51 |
| 2007/0043353 | A1* | 2/2007 | Dycus | A61B 18/00 606/51 |
| 2007/0173814 | A1* | 7/2007 | Hixson | A61B 18/1445 606/51 |
| 2007/0175949 | A1* | 8/2007 | Shelton, IV | A61B 17/07207 227/176.1 |
| 2009/0202387 | A1 | 8/2009 | Dlugos, Jr. et al. | |
| 2012/0080503 | A1* | 4/2012 | Woodard, Jr. | A61B 90/92 227/181.1 |
| 2013/0267951 | A1* | 10/2013 | Twomey | A61B 18/1445 606/46 |

* cited by examiner

*Primary Examiner* — Alexander J Orkin
(74) *Attorney, Agent, or Firm* — Mintz Levin Cohn Ferris Glovsky and Popeo, P.C.

(57) ABSTRACT

Methods and devices are provided having a locking mechanism configured to selectively prevent actuation of the surgical device, e.g., opening and closing of jaws at a distal end of the device, moving a cutting element of the device, etc. In an exemplary embodiment, a device is provided having a closure lever actuator that can move between an open position and an actuated position, thereby opening and closing, respectively, jaws at the distal end of the device. In addition, the device can include a knife trigger that is configured to move a cutting element through the jaws. The device can further include a knife lockout feature that can prevent actuation of the knife trigger until the closure lever is in the actuated position.

17 Claims, 6 Drawing Sheets

SURGICAL DEVICE WITH KNIFE LOCKOUT

FIELD

Methods and devices are provided for treating tissue, and in particular, methods and devices having a knife lockout mechanism are provided.

BACKGROUND

Endoscopic surgical instruments are often preferred over traditional open surgical devices since a smaller incision, or incisions, associated with endoscopic surgical techniques tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applies, access device, drug/gene therapy delivery device, and energy device using ultrasound, RF, laser, etc.).

Some minimally invasive procedures can require cutting of tissue using a cutting feature located at a working end of a device. For example, many surgical stapling devices or energy devices utilize a knife to cut tissue engaged between a pair of jaws. It is undesirable, however, to cut the tissue prior to stapling or sealing the tissue with energy. In addition, inadvertent or improper activation of the cutting feature can result in damage or malfunction of the cutting feature.

Accordingly, there remains a need for improved methods and devices for controlling the ability to activate a cutting feature of a surgical instrument.

SUMMARY

Various methods and devices are provided having one or more features for controlling use of a cutting feature. In one embodiment, a surgical device is provided and includes a handle having an elongate shaft extending distally therefrom. In addition, the surgical device includes an end effector at a distal end of the elongate shaft having first and second jaws that are movable between an open configuration and a closed configuration in which the first and second jaws are configured to engage tissue therebetween. The surgical device can further include a closure lever coupled to the handle and movable from an open position to an actuated position to move the first and second jaws from the open configuration to the closed configuration. A knife trigger can be coupled to the handle and it can be configured to move a cutting element through the first and second jaws, and a knife lockout can be disposed within the handle such that it prevents actuation of the knife trigger until the closure lever is in the actuated position, and such that it allows release of the closure lever prior to release of the knife trigger.

The knife lockout can have a variety of configurations. In one embodiment, the knife lockout includes a lockout engagement face positioned to abut a trigger engagement face of the knife trigger when the closure lever is in the open position to thereby block movement of the knife trigger. The lockout engagement face can extend substantially parallel to the trigger engagement face when the closure lever is in the open position. In other aspects, the device can be configured such that movement of the closure lever into the actuated position can cause the knife lockout to move to an unlocked position to allow actuation of the knife trigger. The surgical device can further include a knife lockout return spring disposed in the handle and configured to bias the knife lockout into a locked position in which the knife lockout prevents actuation of the knife trigger. The surgical device can also include a lever lock disposed in the handle and configured to engage the closure lever for securing the closure lever in the actuated position. For example, the closure lever can include a locking track having a first ramped surface positioned to allow a lever locking feature on the lever lock to travel therealong as the closure lever moves into the actuated position. The lever locking feature can travel past the first ramped surface as the closure lever moves into the actuated position and it can engage a back side of the locking track such that the closure lever is prevented from moving into the open position. The surgical device can further include a lever lock return spring disposed in the handle and positioned to bias the lever locking feature away from the locking track such that the closure lever is allowed to move into the open position. The locking track can include a second surface opposite to the first ramped surface that the lever lock rides adjacent to as the lever locking feature uncouples from the locking track.

In another embodiment, the surgical device can include a handle having an elongate shaft extending distally therefrom and an end effector at a distal end of the elongate shaft. The elongate shaft can have first and second jaws that are movable between an open configuration and a closed configuration in which the first and second jaws are configured to engage tissue therebetween. In addition, the surgical device can include a closure lever coupled to the handle and movable between an open position and an actuated position. Movement of the closure lever between the open position and the actuated position can effect movement of the jaws between the open and closed configurations. The surgical device can further include a knife advancing assembly having a knife trigger coupled to the handle and configured to move a cutting element through the first and second jaws. The knife advancing assembly can further include a rack and gear assembly coupled between the knife trigger and the cutting element for moving the cutting element. A knife lockout can be disposed within the handle and configured to directly contact and engage a gear of the rack and gear assembly to prevent rotation of the gear when the closure lever is in the open position.

In one aspect, the knife lockout can include a gear rotation track and a gear locking track and the gear can include an extension that engages the gear locking track when the closure lever is in the open position and that engages the gear rotation track when the closure lever is in the actuated position. The gear rotation track can be shaped to allow the extension to travel there along as the gear rotates. The gear locking track can be shaped to prevent the extension from moving and thereby prevents the gear from rotating.

Methods for treating tissue are also provided. In one embodiment, the method can include positioning tissue between first and second jaws of a surgical device. A closure lever can be advanced towards a handle of the surgical device thereby closing the first and second jaws to engage the tissue and thereby moving a knife lockout disposed in the handle from a locked position, in which the knife lockout blocks movement of the knife trigger, to an unlocked position, in which the knife lockout allows actuation of a knife trigger. The method can further include activating the knife trigger to move a cutting element through the first and second jaws thereby cutting the tissue engaged between the first and second jaws.

In certain aspects, a lockout engagement face of the knife lockout can contact a trigger engagement face of the knife trigger to block movement of the knife trigger when the knife lockout is in the locked position. The closure lever can include an extension that causes the knife lockout to pivot and move from the locked position to the unlocked position as the closure lever is advanced. In other aspects, a knife lockout return spring disposed in the handle can bias the knife lockout into the locked position to prevent actuation of the knife trigger. The closure lever can include a lever lock that engages the handle to maintain the closure lever in an actuated position when the closure lever is advanced toward the handle. After the knife trigger is activated, the closure lever can be advanced toward the handle to cause the lever lock to release the closure lever. The method can further include activating a power source located on the handle to apply energy to the tissue engaged between the first and second jaws.

In another embodiment, a method can include positioning tissue between first and second jaws of a surgical device. In addition, the method can include advancing a closure lever towards a handle of the surgical device thereby closing the first and second jaws to engage the tissue and thereby moving a knife lockout disposed in the handle from a locked position, in which the knife lockout blocks rotation of a gear, to an unlocked position, in which the knife lockout allows rotation of the gear. The method can further include activating the knife trigger to move the gear, thereby moving a cutting element through the first and second jaws thereby cutting the tissue engaged between the first and second jaws.

The present disclosure further provides devices and methods as claimed.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

When practical, similar reference numbers denote similar structures, features, or elements.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods and devices for actuating surgical instruments are provided. In general, a surgical device can include one or more actuators and locking features configured to selectively prevent actuation of the device, e.g., articulation of an end effector of the device, opening and closing of jaws at a distal end of the device, moving a cutting element of the device, etc. In an exemplary embodiment, the device can include a closure lever actuator that is coupled to a handle of the device. The closure lever can move between an open position and an actuated position to open and close, respectively, jaws at the distal end of the device. In addition, the device can include a knife trigger that is configured to move a cutting element through the jaws. The device can further include a knife lockout feature that can prevent actuation of the knife trigger until the closure lever is in the actuated position. The knife lockout can also allow the closure lever to be released from the actuated position prior to release of the knife trigger from the actuated position.

Figure 1:
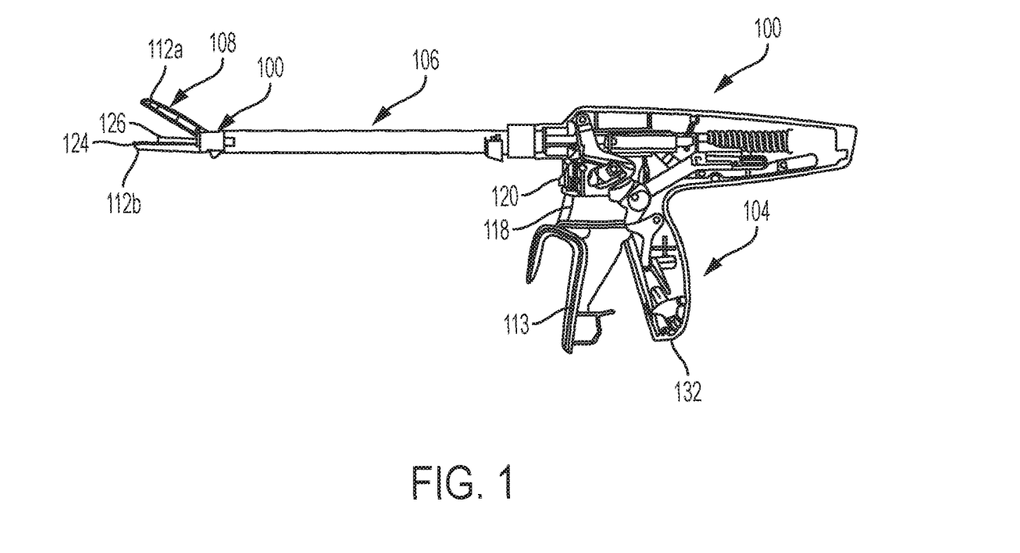
FIG. 1 is a side, partially transparent view of one embodiment of a surgical device.

FIG. 1 illustrates one embodiment of a surgical device 100 that includes a proximal handle portion 104 having a shaft assembly 106 extending distally therefrom. The device 100 includes a working element 108, also referred to herein as an "end effector," coupled to a distal end of the shaft assembly 106. The end effector 108 can have a variety of sizes, shapes, and configurations. As shown in FIG. 1, the end effector 108 includes first and second jaws 112a, 112b disposed at a distal end of the surgical device 100. The end effector 108 in the illustrated embodiment is in the form of a tissue grasper having a pair of opposed jaws 112a, 112b that are pivotally coupled to one another and are configured to move between open and closed configurations. In the illustrated embodiment, the first or upper jaw 112a pivots while the second or lower jaw 112b remains stationary. In other embodiments, only the second jaw 12b may move or both jaws 112a, 112b may move. The end effector 108 can have other configurations, e.g., scissors, a Babcock, a retractor, etc.

One or both of the jaws 112a, 112b can also include electrodes 124, which can be configured to contact tissue positioned between the jaws 112a, 112b and to apply energy thereto. The electrodes 124 are arranged longitudinally along the tissue-contacting surface of the bottom jaw 112b in the illustrated embodiment, however, the electrodes 124 can be arranged in any of a variety of ways on the upper jaw 112a and/or the lower jaw 112b. The electrodes 124 can be configured to apply energy to tissue, such as radiofrequency (RF) or ultrasound energy. The handle portion 104 of the device 100 can be configured to couple to an energy source, such as by connecting to a generator, to supply energy to the electrodes 124 via one or more leadings extending from the handle 104 and through the shaft assembly 106.

The handle portion 104 can have a variety of sizes, shapes, and configurations. The illustrated handle portion 104 includes a main housing 132, which houses a variety of elements therein and can have some elements accessible outside thereof, such as a first actuator 113, a second actuator 118, and a third actuator 120.

The first actuator 113 can be configured to effect the opening and closing of the opposed jaws 112a, 112b, e.g., movement of the jaws 112a, 112b toward and away from one another. The jaws 112a, 112b in FIG. 1 are shown in the open position. In an exemplary embodiment, the first actuator 113 is in the form of a handle or closure lever. The closure lever 113 can, in other embodiments, have different sizes, shapes, and configurations, e.g., no thumb rests, multiple finger loops, different arcuate shape, etc. The closure lever 113 is pivotally coupled to the main housing 132 and it is configured to pivot about a lever pivot point 114 (FIG. 3) that allows the closure lever 113 to move toward and away from the main housing 132 to cause opening and closing of the end effector 108.

The second actuator 118, which is also referred to herein as a "knife trigger," can be configured to translate a cutting element 126 (e.g., a knife, a blade, etc.) along the end effector 108. The cutting element 126 can be configured to cut tissue positioned between the jaws 112a, 112b, as will be appreciated by a person skilled in the art. In some implementations, for example, the jaws 112a, 112b can include an elongate slot 128 therein through which the cutting element 126 can be configured to slide.

Figure 2A:
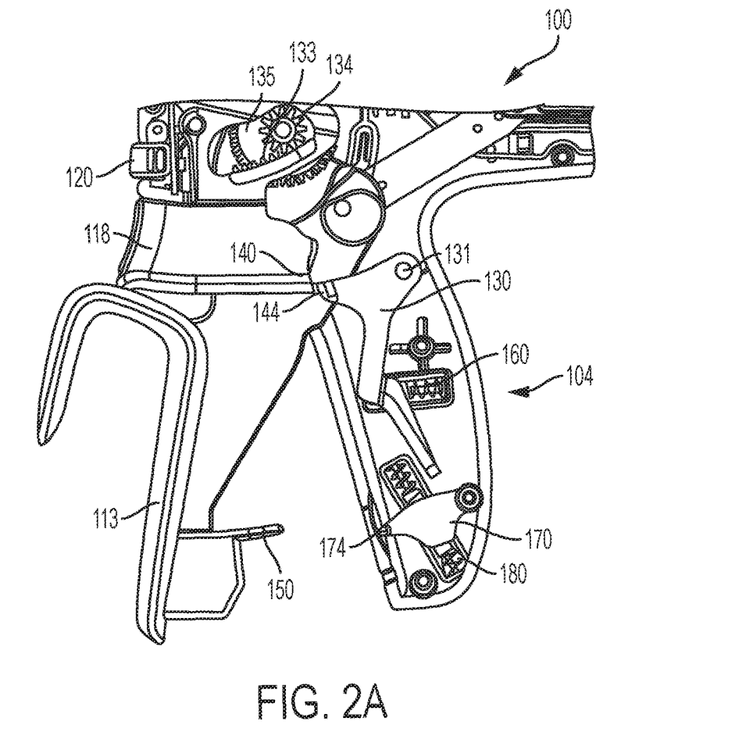
FIG. 2A is a side, partially transparent view of a handle portion of the surgical device of FIG. 1 with a knife lockout in a locked configuration, a closure lever in an open position, and a knife trigger in a non-actuated position.

The third actuator 120 can be configured to turn on and off the application of the energy, which can be delivered to tissue via the electrodes 124. The third actuator 120, as shown in FIGS. 1 and 2A, is in the form of a button, however, the third actuator 120 can have other configurations, e.g., a knob, a lever, a movable handle, a switch, etc. In other embodiments, the surgical device need not be configured to apply energy to tissue.

Figure 2B:
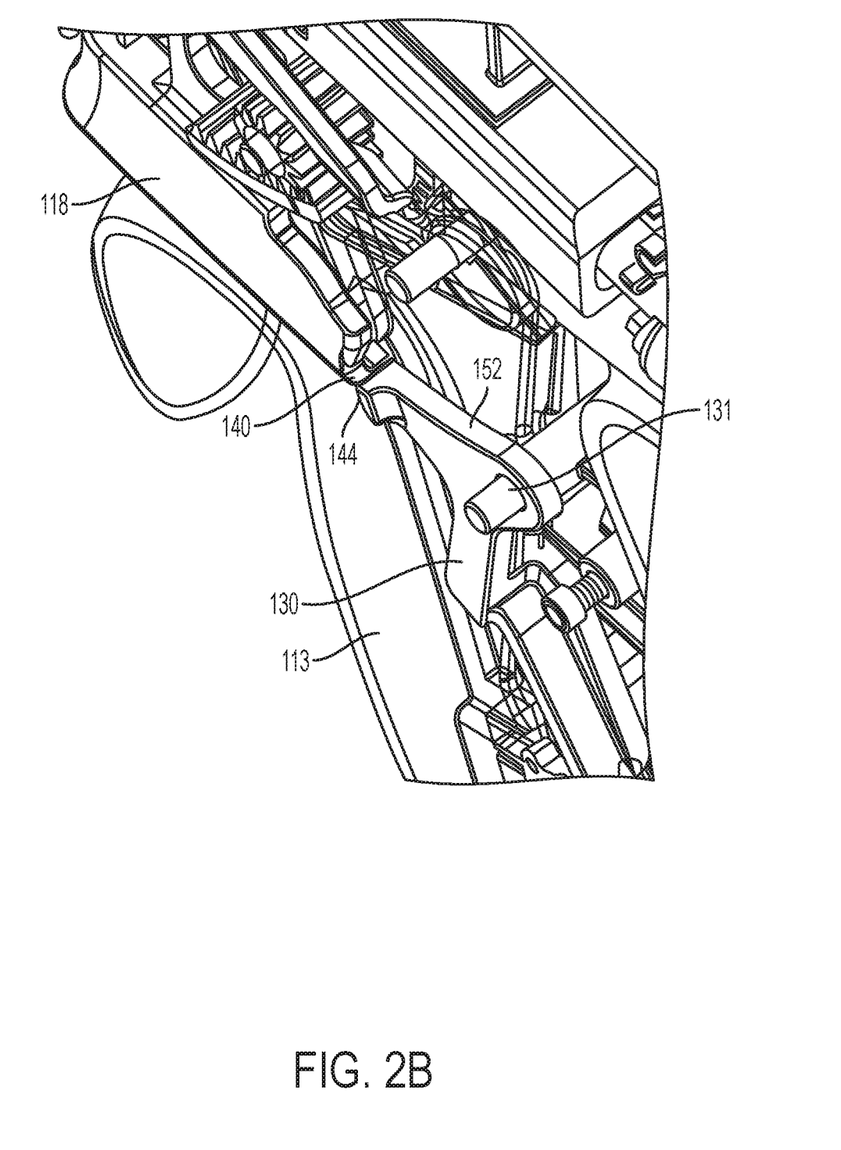
FIG. 2B is a top, partially transparent view of the handle portion of the surgical device of FIG. 2A showing a lockout engagement face of the knife lockout positioned to mate with and prevent movement of a trigger engagement face of the knife trigger.
Figure 3:
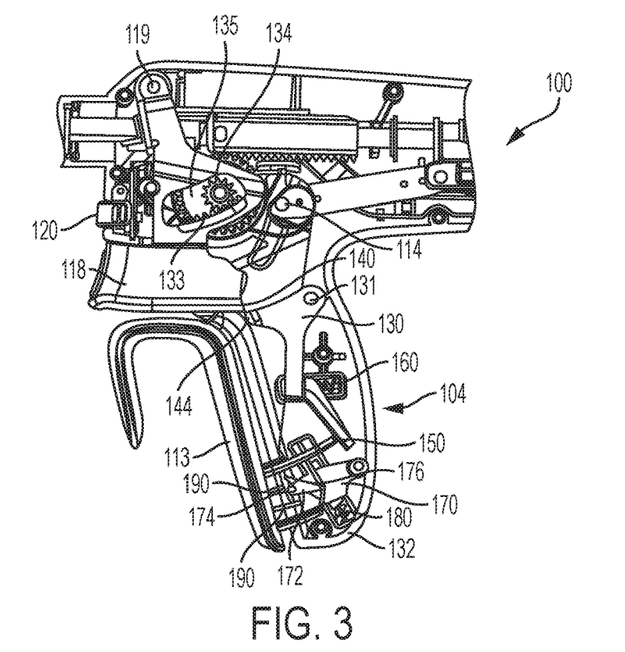
FIG. 3 is a side, partially transparent view of the handle portion of the surgical device of FIG. 1 with the knife lockout in an unlocked configuration, the closure lever in a closed position, and the knife trigger in a non-actuated position.
Figure 4:
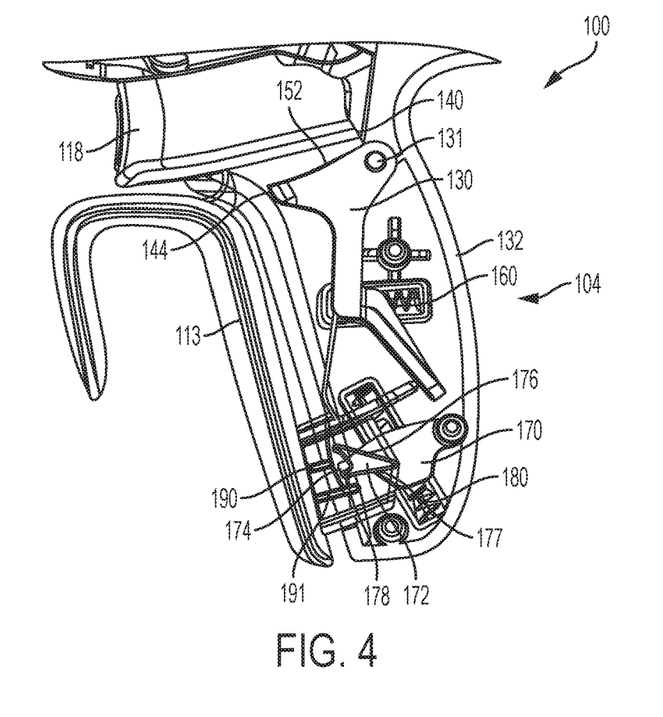
FIG. 4 is a side, partially transparent view of the handle portion of the surgical device of FIG. 1 with the knife lockout in an unlocked configuration, the closure lever in a closed position, and the knife trigger in an actuated position.
Figure 5:
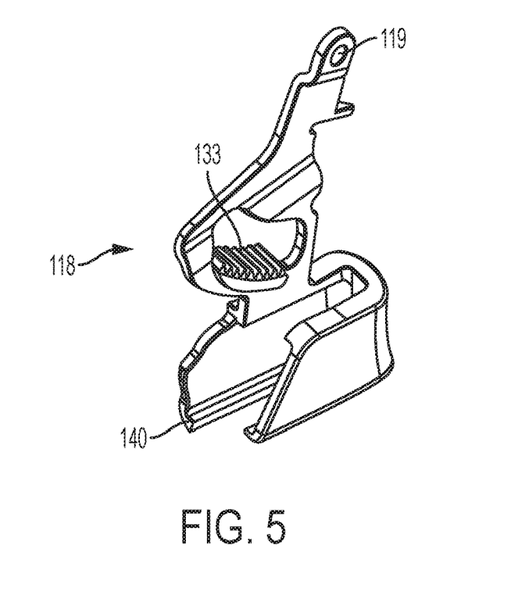
FIG. 5 is a perspective view of the knife trigger of the surgical device of FIG. 1.

FIGS. 1-4 and 6 illustrate a knife lockout 130 that can be disposed within the handle 104 to control the actuation of the knife trigger 118. For example, the knife lockout 130 can prevent actuation of the knife trigger 118 until the closure lever 113 is in the actuated or closed position (as shown in FIGS. 3 and 4). In this way, a user of the device 100 is prevented from actuating the cutting element 126 until the jaws 112a, 112b are closed. When the jaws 112a, 112b are closed, tissue is secured between the jaws 112a, 112b thereby allowing the cutting element 126 to effectively advance and cut through the tissue. Once the cutting element 126 has been advanced (i.e., the knife trigger 118 has been actuated), it can be desirable to initiate opening of the jaws 112a, 112b just before retracting the cutting element 126. The knife lockout 130 disclosed herein can both prevent the actuation of the cutting element 126 until the jaws 112a, 112b are closed, as well as allow the jaws 112a, 112b to open before retracting or de-actuating the cutting element 126, as will be discussed in greater detail below.

As shown in FIGS. 1-4 and 6, the knife lockout 130 includes an elongated body having a top end that engages with the knife trigger 118 when the knife lockout 130 is in the locked configuration (as shown in FIGS. 2A and 2B) and a bottom end that engages with the closure lever 113 when the closure lever 113 is in the actuated position (as shown in FIGS. 3 and 4). The top end of the knife lockout 130 includes a lockout engagement face 144 that is positioned and configured to engage a trigger engagement face 140 of the knife trigger 118, as shown in FIGS. 2A and 2B. A first pivot point 131 is located along the elongated body of the knife lockout 130 such that movement or pivoting of the bottom end of the knife lockout 130 causes the top end to also move or pivot. As such, pivoting of the bottom end of the knife lockout 130 in a proximal direction can cause the top end to pivot down and move out of the way of the knife trigger 118 (i.e., the knife lockout 130 is in the unlocked configuration), thereby allowing the knife trigger 118 to be actuated.

The knife lockout 130 can be forced to move from the locked configuration to the unlocked configuration in one or more of a variety of ways. As shown in FIGS. 2-4, the closure lever 113 can include an engagement feature 150 that extends towards the handle 104. When the closure lever 113 is in the open position, the engagement feature 150 does not come into contact with the handle 104. However, upon closure of the closure lever 113 (i.e., actuation of the closure lever 113), the engagement feature 150 engages the bottom end of the knife lockout 130, thereby forcing the knife lockout 130 to pivot proximally into the unlocked configuration. For example, the engagement feature 150 can engage and proximally move the bottom end of the knife lockout 130, which can cause the knife lockout 130 to pivot along the first pivot point 131 and cause the lockout engagement face 144 to pivot down and move out of the way of the trigger engagement face 140. Once the lockout engagement face 144 is out of the way of the trigger engagement face 140, the knife trigger 118 is allowed to be actuated and moved proximally into the housing to advance and actuate the cutting element 126.

The device can further include a lever lock 170 that is disposed in the handle 104 for releasably engaging the closure lever 113. For example, as shown in FIG. 4, the closure lever 113 can include a locking track 172 that can assist with allowing the lever lock 170 to engage the closure lever 113, thereby securing the closure lever 113 in the actuated position. This can assist with securing the closure lever in the actuated position (with the jaws 112a, 112b closed) while cutting tissue. It can be desirable to keep the jaws 112a, 112b closed while cutting to prevent bending or breaking of the cutting element 126. The lever lock 170 can automatically lock the closure lever 113 in the actuated position once the closure lever 113 has entered the actuated position. In addition, in order to unlock the closure lever 113 from the actuated position, the user may need to perform an additional action. In this way, the user can control the locking and unlocking of the closure lever 113 from the actuated position.

As shown in FIG. 4, the locking track 172 of the closure lever 113 can engage and secure a lever locking feature 174 of the lever lock 170 for releasably securing the lever lock 170 to the locking track 172 and thereby releasably securing the closure lever 113 in the actuated position. The lever locking feature 174 can be in the form of an extension or protrusion, an extruded feature, or the like, and can have a variety of shapes and/or sizes. In the illustrated embodiment, the locking track 172 is defined by a substantially triangular protrusion formed within the closure lever 113. The locking track 172 includes a first ramped surface 176 formed along the top of the substantially triangular protrusion and positioned to allow the lever locking feature 174 of the lever lock 170 to travel therealong as the closure lever 113 moves into the actuated position. The lever locking feature 174 can travel along and past the first ramped surface 176 as the closure lever 113 moves into the actuated position. Once past the first ramped surface 176, the lever locking feature 174 can drop down and engage a concavity or pocket 178 formed in a back side of the protrusion defining the locking track 172. Once engaged with the pocket 178 of the locking track 172, the closure lever 113 is prevented from moving into the open position.

In some implementations, the device 100 can include a lever lock return spring 180 that is disposed in the handle 104 and positioned adjacent the lever lock 170 for applying a spring force against the lever lock 170. For example, the lever lock return spring 180 can apply a spring force against the lever lock 170 such that it encourages the lever lock 170 to move in a first direction (i.e., towards a base of the handle 104). As such, the first ramped surface 176 can be configured such that it increases in height distally in a second direction (i.e., away from the base of the handle 104). The lever locking feature 174 will ride up and along the first ramped surface against the spring force in the first direction as the closure lever closes. At the end of the first ramped surface 176, the lever locking feature 174 can travel past the first ramped surface 176 and the spring force will force the lever lock 170 in the first direction, causing it to drop below the end of the first ramped surface 176 and become engaged with the pocket 178 as the closure lever 113 moves into the actuated position and as a result of the lever lock return spring 180.

When the lever lock feature 174 is engaged with the pocket 178 of the locking track, the closure lever 113 is prevented from moving out of the actuated position. This can also allow the user of the device 100 to not have to apply a force (such as a gripping force) against the closure lever 113 in order to maintain the closure lever 113 in the actuated position. However, when the user would like to release the closure lever 113 from the actuated position, the closure lever 113 can be advanced slightly towards the handle 104 to allow the lever lock feature 174 to become disengaged from the pocket 178. For example, once the lever lock feature 174 is engaged with the pocket 178 of the locking track 172, advancing the closure lever 113 towards the handle 104 can allow the lever lock feature 174 to disengage and drop below the pocket 178 (along with the assistance of the lever lock return spring 180 forcing the lever lock 170 in the first direction) and return to a starting position that is free from engagement with the closure lever 113. As such, the closure lever 113 can then return to the open position. As the closure lever 113 returns to the open position, the lever lock feature 174 can move adjacent a second surface 177 of the locking track 172. As shown in FIG. 4, the second surface 177 is formed on the bottom of the substantially triangular protrusion and it is substantially flat and aligned substantially parallel to the direction of the movement of the closure lever 113 as the closure lever 113 moves into the open configuration. As such, the second surface 177 allows the lever lock feature 174 to travel past the locking track 172, thereby allowing the closure lever 113 to move into the open configuration.

In some implementations, the closure lever 113 can include one or more extruded guides 190 that can assist with ensuring that the lever lock feature 174 becomes engaged with the locking track 172. For example, as shown in FIG. 4, the closure lever 113 can include a first extruded guide 190 that can prevent the lever lock feature 174 from dropping past the pocket 178, as well as provide a guide along which the lever lock feature 174 can advance along before becoming engaged with the pocket 178. The closure lever 113 also includes a second extruded guide 191 that guides the lever lock feature 174 along the second surface 177 as the closure lever 113 is being released to the open position. The closure lever 113 can include one or more of such extruded guides 190 for assisting the lever lock feature 174 with either engaging with or disengaging from the locking track 172. In addition, the locking track 172 and/or extruded guides 190 can have any number of shapes and sizes for assisting with securing and releasing the closure lever 113 from the actuated position.

With reference to FIGS. 2-4, the knife lockout 130 is disposed in the handle 104 and is in the form of an elongated, substantially T-shaped body that is pivotably engaged with the handle 104 at the first pivot point 131. As explained above, the knife lockout 130 can pivot about the first pivot point 131, which can allow the knife lockout 130 to move between the locked and unlocked configurations. As also indicated above, the knife lockout 130 can include a lockout engagement face 144 that is configured to engage with a part of the knife trigger for preventing the knife trigger 118 from being actuated when the knife lockout 130 is in the locked configuration. For example, in the locked configuration, the lockout engagement face 144 of the knife lockout 130 is aligned with and mated with the trigger engagement face 140 of the knife trigger 118, thereby preventing pivotal movement and actuation of the knife trigger 118, as shown in FIG. 2. In the unlocked configuration, the knife lockout 130 is positioned such that the lockout engagement face 144 is neither aligned with nor mated with the trigger engagement face 140 of the knife trigger 118, thereby allowing the knife trigger 118 to move and actuate the cutting element, as shown in FIG. 4.

As shown in FIG. 2B, the lockout engagement face 144 of the knife lockout 130 can have an increased width such that the knife lockout 130 has a greater surface area than other parts of the knife lockout, such as for providing a greater engagement surface area between the lockout engagement face 144 and the trigger engagement face 140 of the knife trigger 118. Since the lockout engagement face 144 and the trigger engagement face 140 extend substantially parallel to one another when the closure lever 113 is in the open position, the increased width of the lockout engagement face 144 will prevent the trigger engagement face 140 from becoming mis-aligned and sliding past the lockout engagement face 144. This can allow for a secure engagement between the knife lockout 130 and the knife trigger 118, thereby allowing the knife lockout 130 to prevent actuation of the knife trigger 118 when the knife lockout 130 is in the locked configuration.

As shown in FIGS. 3 and 4, a top surface 152 of the knife lockout 130 can have a concave curvature to allow the knife trigger 118 to move above the top surface 152 when the knife lockout 130 is in the unlocked configuration. In addition, the concave curvature of the top surface 152 can allow the knife trigger 118 to slide along the top surface of the knife lockout 130, such as when the closure lever 113 is in the open configuration and no longer forcing the knife lockout 130 in the unlocked position.

Figure 6:
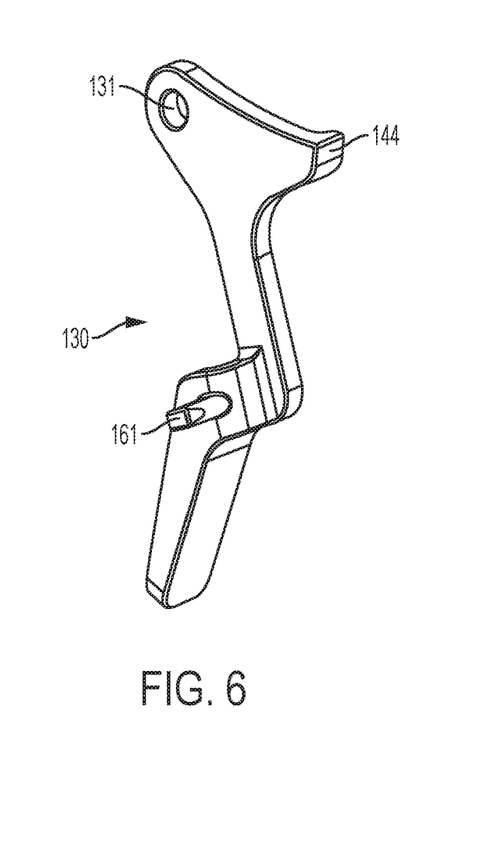
FIG. 6 is a perspective view of the knife lockout of the surgical device of FIG. 1.

The device 100 can also include a knife lockout return spring 160 that is positioned to apply a distally-directed spring force on an end or feature (such as an extruded feature 161, as shown in FIG. 6) of the knife lockout 130, thereby encouraging the knife lockout 130 to return to the locked configuration. The spring force of the knife lockout return spring 160 can be great enough to encourage and force the knife lockout 130 to move to the locked configuration when the closure lever 113 is in the open position. However, the spring force of the knife lockout return spring 160 can also allow the knife lockout 130 to pivot into the unlocked configuration, such as when the closure lever 113 is moved to the actuated or closed position.

Figure 7:
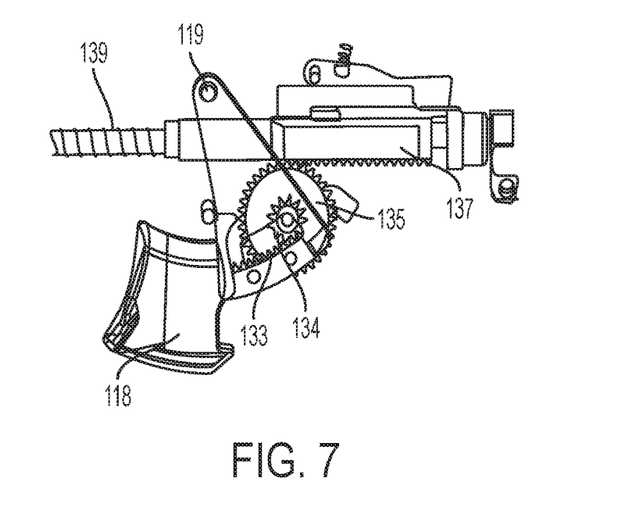
FIG. 7 is a first side, partially transparent view of the knife trigger, a gear assembly, and a rack that assist in actuating a cutting element of the surgical device of FIG. 1.

As shown in FIGS. 2-5, the knife trigger 118 is in the form of an elongated body that extends into the handle 104. The knife trigger 118 can pivot about a second pivot point 119 when actuated. As shown in FIG. 7, the knife trigger 118 can have an opening formed therein with one or more teeth 133 that can engage with teeth on a first gear 134 associated with a gear assembly that assists with moving the cutting element 126, such as when the knife trigger 118 is actuated. For example, when the knife trigger 118 is actuated and pivots about the second pivot point 119, the teeth 133 can force the first gear 134 to rotate. As shown in FIG. 7, the first gear 134 is coupled to a second gear 135 that engages a rack 137 such that when the first gear 134 is forced to rotate, the second gear 135 rotates and causes the rack 137 to move in a distal linear direction to an actuated position, thereby distally advancing the cutting element 126 through the jaws. A rack return spring 139 can apply a proximal biasing force against the rack 137, such that when the knife trigger 118 is released, the rack return spring 139 can force the rack 137 to return to a proximal starting position, thereby causing the first and second gears 134, 135 to rotate and the knife trigger 118 to return to a starting position.

During use of the device 100, for example, tissue can be positioned between the jaws 112a, 112b for securing the tissue therebetween. The closure lever 113 can then be advanced towards the handle, thereby closing the first and second jaws 112a, 112b to engage the tissue and thereby move the knife lockout 130 to the unlocked position. Once the knife lockout 130 is in the unlocked position, the knife trigger 118 can be activated. Activation of the knife trigger 118 can move the cutting element 126 through the jaws 112a, 112b thereby cutting the tissue engaged between the jaws 112a, 112b.

The closure lever 113 can be locked in the actuated position via engagement of the lever lock feature 174 of the lever lock 170 with the pocket 178 of the locking track 172. To release the closure lever 113 from the actuated position, the closure lever 113 can be advanced towards the handle to allow disengagement between the lever lock feature 174 and the pocket 178. Once disengaged, the closure lever 113 can return to the open position, thereby opening the first and second jaws 112a, 112b.

Figure 8:
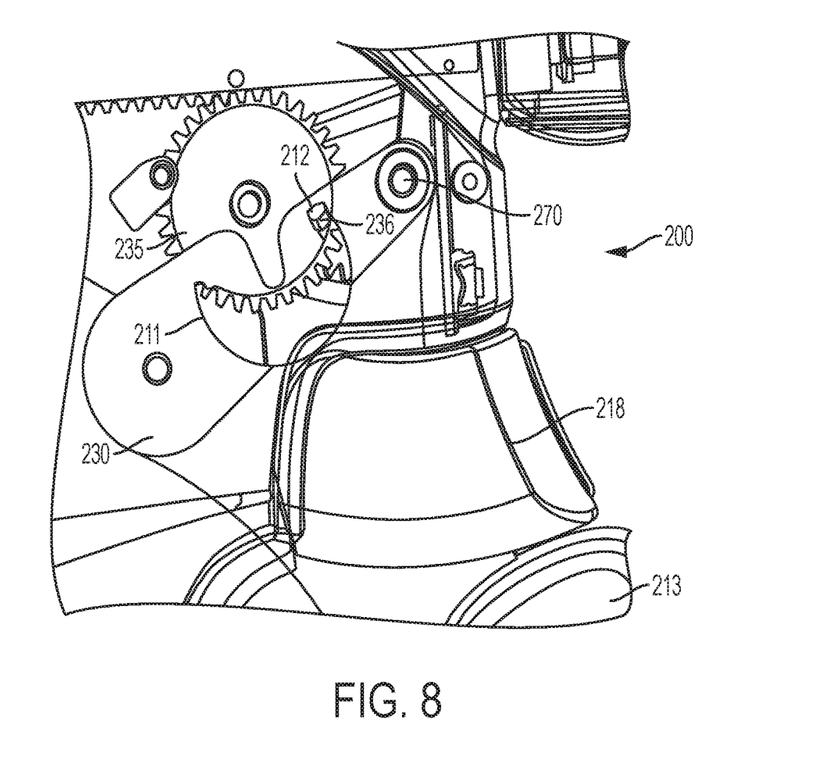
FIG. 8 is a second side, partially transparent view of another embodiment of a surgical device, including a knife lockout having a gear rotation track and a gear locking track, with the knife lockout being shown in the locked configuration.
Figure 9:
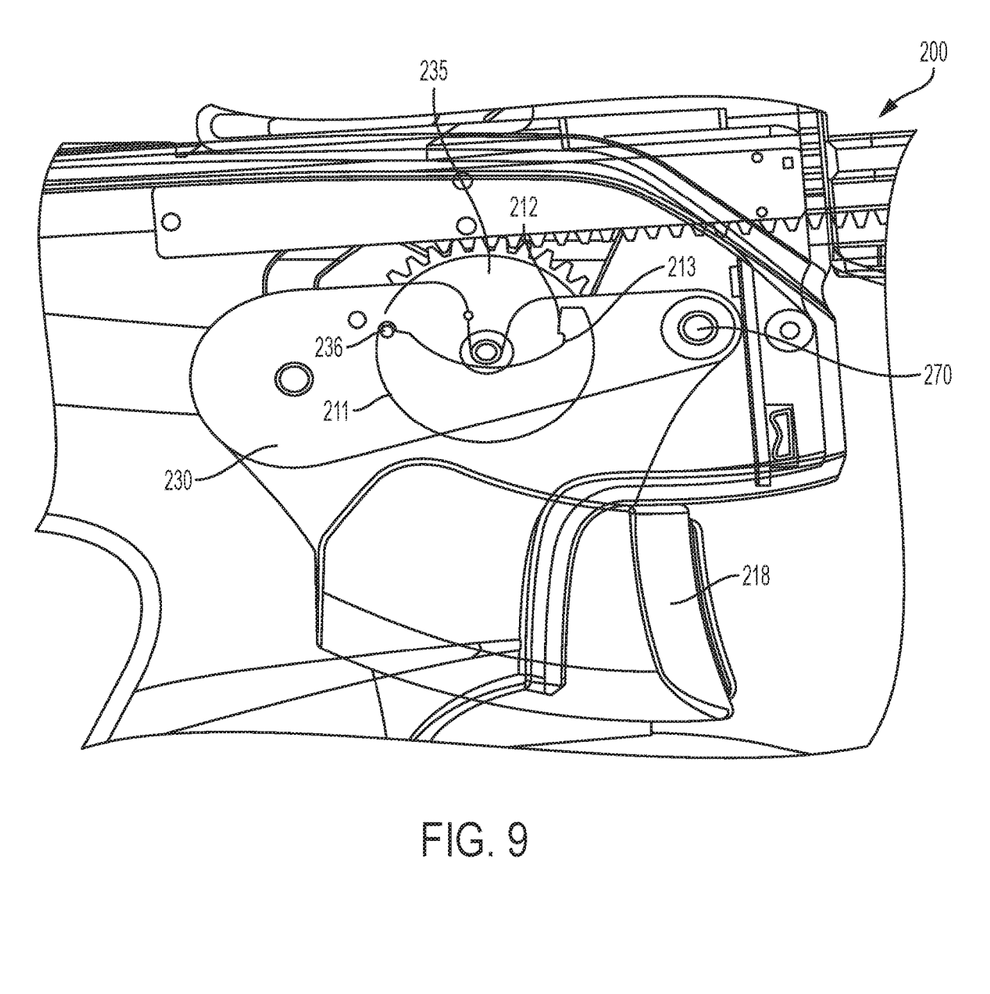
FIG. 9 is a side, partially transparent view of the surgical device of FIG. 8 with the knife lockout in an unlocked configuration.

FIGS. 8-9 illustrate another embodiment of a surgical device 200. The device 200 can generally be configured and used similar to the surgical device 100 of FIGS. 1-7, such as the same or similar shaft assembly, end effector, knife trigger, and handle configuration. As will be described in greater detail below, in this embodiment the device 200 includes a knife lockout 230 that directly engages a gear assembly to prevent the knife trigger (and cutting element) from being actuated prior to the closure lever 213 being in a closed or actuated position.

As shown in FIGS. 8-9, a knife lockout 230 is included in the device to control movement of the gears that drive the cutting element, thereby controlling actuation of the knife trigger 118 and movement of the cutting element. While not shown in FIGS. 8 and 9, the knife trigger 218 can be configured similar to knife trigger 118 discussed above. In particular, as shown in FIG. 7 and discussed above, the knife trigger 118 can have an opening formed therein with one or more teeth 133 that can engage with teeth on a first gear 134 associated with a gear assembly. When the knife trigger 118 is actuated and pivots about the second pivot point 119, the teeth 133 can force the first gear 134 to rotate, thereby causing the second gear 135 rotate and the rack 137 to move in a distal linear direction to an actuated position, which advances the cutting element 126 through the jaws 112a, 112b.

The knife lockout 230 can have a locked configuration and an unlocked configuration. In the locked configuration, the knife lockout 230 can directly engage and prevent the second gear 135 from rotating, thereby preventing the knife trigger 118 from being actuated. In the unlocked configuration, the knife lockout 230 can allow the second gear 135 to rotate, thereby allowing the knife trigger 118 to be actuated. As shown in FIGS. 8-9, the knife lockout 230 can include a cutout that defines both a gear rotation track 211 and a gear locking track 212. The second gear 235 can include an extension 236 that extends through the cutout of the knife lockout 230 such that it can be positioned within the gear rotation track 211 or the gear locking track 212, depending on the position of the closure lever 213. When the extension 236 is disposed within the gear rotation track 211, the second gear 135 is allowed to rotate. When the extension 236 is disposed within with the gear locking track 212, the second gear 135 is prevented from rotating.

As shown in FIGS. 8-9, the gear rotation track 211 can be semi-circular in shape which can provide a circular pathway for the extension 236 to move along as the second gear 135 rotates. As such, when the extension 236 is positioned within the gear rotation track 211 (i.e., the knife lockout 230 is in the unlocked configuration), the knife trigger 218 can be actuated. In contrast, the gear locking track 212 can be in the form of a notch or groove such that it prevents the extension 236 from moving when the extension 236 is disposed therein, thereby preventing the second gear 135 from rotating. In particular, the notch or groove can result in a blocking surface 237 that extends proximally and beneath the extension 236 when the extension 236 is disposed within the gear locking track 212, as shown in FIG. 8. As such, any attempt to actuate the knife trigger 218 and thus rotate the second gear 235 in a clockwise direction will cause the extension 236 to abut against the blocking surface 237. The blocking surface 237 will thus prevent clockwise rotation of the second gear 235, thereby preventing actuation of the knife trigger 218. Thus, when the extension 236 is engaged with the gear locking track 212 (i.e., the knife lockout 230 is in the locked configuration), the knife trigger 118 is prevented from being actuated and the cutting element is prevented from traveling through the jaws 112a, 112b.

In some implementations, the knife lockout 230 can form the upper portion of the closure lever 213, as shown in FIGS. 8-9. However, in some implementations, the knife lockout 230 can be a separate element that can be acted upon by the closure lever 213. In either instance, movement of the closure lever 213 between the open position, where the jaws are open, and the actuated position, where the jaws are closed, can be effective to move the cut-out, and thus the tracks 211, 212 defined therein, relative to the extension 236 on the second gear 235. In particular, when the closure lever 213 is in the open position, the knife lockout 230 can be positioned such that the extension 236 of the second gear 135 is engaged with the gear locking track 212, as shown in FIG. 8. When the closure lever 213 and knife lockout 230 pivot along pivot point 270 towards the handle, the closure lever 213 moves into the actuated position which causes the knife lockout 230 to move upward into the unlocked position. The cut-out will thus move upward to thereby position the extension 236 within the gear rotation track 211. As discussed above, the semi-circular shape of the gear rotation track 211 extends a distance to allow the extension 236 to move freely along the semi-circular gear rotation track 211, thereby allowing the second gear 135 to rotate. As such, once the closure lever 213 is in the actuated position, the second gear 135 can be allowed to rotate, thereby allowing the knife trigger 218 to be actuated and the cutting element to advance.

Furthermore, the gear rotation track 211 can be shaped such that once the knife trigger 218 has been actuated, the closure lever 213 can be allowed to return or partially return to the open position while the knife trigger 218 remains in the actuated or partially actuated position. For example, as shown in FIGS. 8-9, the gear rotation track 211 can be crescent shaped such that it allows the closure lever 213 to be in either the open or actuated position (or anywhere therebetween) while still allowing the knife trigger 218 to be maintained in the actuated position. The crescent shape of the gear rotation track 211 can provide various arced pathways for the extension 236 to travel along within the gear rotation track 211, thus allowing various orientations between the locking track 230 and the second gear 235 in which the second gear 235 is allowed to rotate. The shape of the gear rotation track 211 can also allow the knife trigger 218 to move back into the non-actuated position when the closure lever 213 is in either the open or actuated position. As such, once the closure lever 213 has moved to the actuated position and the knife lockout 230 has moved into the unlocked position, the gear rotation track 211 can allow for opening and closing of the jaws 112a, 112b (via moving the closure lever 213 into the actuated and open positions, respectively). However, once the knife lockout 230 is moved back into the non-actuated position when the closure lever 213 is also in the open position, the extension 236 is reset in the locked position where the extension 236 is engaged with the gear locking track 212 and the blocking surface 237 prevents clockwise rotation of the second gear 235, thereby preventing actuation of the knife trigger 218.

A person skilled in the art will appreciate that the present invention has application in conventional minimally-invasive and open surgical instrumentation as well application in robotic-assisted surgery. The devices disclosed herein can also be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. Pub. No. 2009/0202387 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical device, comprising:
   a handle having an elongate shaft extending distally therefrom;
   an end effector at a distal end of the elongate shaft and having first and second jaws that are movable between an open configuration and a closed configuration in which the first and second jaws are configured to engage tissue therebetween;
   a closure lever coupled to the handle and movable from an open position to an actuated position to move the first and second jaws from the open configuration to the closed configuration;
   a knife trigger coupled to the handle and configured to move a cutting element through the first and second jaws; and
   a knife lockout disposed within the handle such that it prevents actuation of the knife trigger until the closure lever is in the actuated position, the knife lockout being positioned proximal to a proximal-most point on the knife trigger to thereby block proximal movement of the knife trigger until the closure lever is in the actuated position, the knife lockout having a distally-facing substantially planar lockout engagement face that abuts a substantially planar trigger engagement face of the knife trigger when the closure lever is in the open position to thereby block proximal movement of the knife trigger.

2. The device of claim 1, wherein the lockout engagement face extends substantially parallel to the trigger engagement face when the closure lever is in the open position.

3. The device of claim 1, wherein the device is configured such that movement of the closure lever into the actuated position causes the knife lockout to move to an unlocked position to allow actuation of the knife trigger.

4. The device of claim 1, further comprising a knife lockout return spring disposed in the handle and configured to bias the knife lockout into a locked position in which the knife lockout prevents actuation of the knife trigger.

5. The device of claim 1, further comprising a lever lock disposed in the handle and configured to engage the closure lever for securing the closure lever in the actuated position.

6. The device of claim 5, wherein the closure lever includes a locking track having a first ramped surface positioned to allow a lever locking feature on the lever lock to travel therealong as the closure lever moves into the actuated position, the lever locking feature traveling past the first ramped surface as the closure lever moves into the actuated position and engaging a back side of the locking track such that the closure lever is prevented from moving into the open position.

7. The device of claim 6, further comprising a lever lock return spring disposed in the handle and positioned to bias the lever locking feature away from the locking track such that the closure lever is allowed to move into the open position.

8. The device of claim 7, wherein the locking track includes a second surface opposite to the first ramped surface that the lever lock rides adjacent to as the lever locking feature uncouples from the locking track.

9. The device of claim 1, wherein the knife lockout is disposed entirely within the handle.

10. A surgical device, comprising:
a handle having an elongate shaft extending distally therefrom;
an end effector at a distal end of the elongate shaft and having first and second jaws that are movable between an open configuration and a closed configuration in which the first and second jaws are configured to engage tissue therebetween;
a closure lever coupled to the handle movable between an open position and an actuated position, movement of the closure lever between the open position and the actuated position being effective to move the jaws between the open and closed configurations; and
a knife advancing assembly having
a knife trigger coupled to the handle configured to move a cutting element through the first and second jaws, and
a rack and gear assembly coupled between the knife trigger and the cutting element for moving the cutting element, and
a knife lockout disposed within the handle and configured to directly contact and engage the knife trigger when the closure lever is in the open position, the knife lockout being configured to rotate out of engagement with the knife trigger when the closure lever is in the actuated position to allow actuation of the knife trigger, the knife lockout including a substantially rectangular lockout engagement face positioned to face distally and abut a substantially rectangular trigger engagement face of the knife trigger when the closure lever is in the open position to thereby block proximal movement of the knife trigger.

11. The device of claim 10, further comprising a lever lock disposed in the handle and configured to engage the closure lever for securing the closure lever in the actuated position.

12. The device of claim 11, wherein the closure lever includes a locking track having a first ramped surface positioned to allow a lever locking feature on the lever lock to travel therealong as the closure lever moves into the actuated position, the lever locking feature traveling past the first ramped surface as the closure lever moves into the actuated position and engaging a back side of the locking track such that the closure lever is prevented from moving into the open position.

13. The device of claim 12, further comprising a lever lock return spring disposed in the handle and positioned to bias the lever locking feature away from the locking track such that the closure lever is allowed to move into the open position.

14. The device of claim 13, wherein the locking track includes a second surface opposite to the first ramped surface that the lever lock rides adjacent to as the lever locking feature uncouples from the locking track.

15. The device of claim 10, wherein the lockout engagement face extends substantially parallel to the trigger engagement face when the closure lever is in the open position.

16. The device of claim 10, wherein the device is configured such that movement of the closure lever into the actuated position causes the knife lockout to move to an unlocked position to allow actuation of the knife trigger.

17. The device of claim 10, further comprising a knife lockout return spring disposed in the handle and configured to bias the knife lockout into a locked position in which the knife lockout prevents actuation of the knife trigger.

* * * * *